United States Patent [19]

Kovács et al.

[11] Patent Number: 5,322,698
[45] Date of Patent: Jun. 21, 1994

[54] PROCESS FOR THE PREPARATION OF A TABLET OR DRAGEE COMPOSITION CONTAINING A HEAT-, LIGHT- AND MOISTURE-SENSITIVE ACTIVE INGREDIENT HAVING MONOCLINIC CRYSTAL STRUCTURE

[75] Inventors: István Kovács; Katalin Beke; Tibor Máthé; Judit Szilágyi; György Bacsa; Katalin Marossy; Sándor Jancsó; Levente Szendrei, all of Debrecen; Erno Orbán, Budapest; Margit Simó, Budapest; Margit Biblo, Budapest; Dorottya Bobák, Budapest; József Langó, Budapest, all of Hungary

[73] Assignee: Biogal Gyogyszergyar Rt., Debrecen, Hungary

[21] Appl. No.: 849,067

[22] PCT Filed: Aug. 23, 1991

[86] PCT No.: PCT/HU91/00039
§ 371 Date: Jun. 5, 1992
§ 102(e) Date: Jun. 5, 1992

[87] PCT Pub. No.: WO92/03126
PCT Pub. Date: Mar. 5, 1992

[30] Foreign Application Priority Data
Aug. 24, 1990 [HU] Hungary ............... 5314/90

[51] Int. Cl.⁵ ............................... A61K 9/36
[52] U.S. Cl. ...................... 424/480; 424/474; 424/475; 424/482; 424/682; 424/686; 424/687; 424/696; 424/697; 514/781; 514/788; 514/960; 514/961; 564/238
[58] Field of Search ............... 424/474, 475, 480, 687, 424/686, 696, 697, 682, 482; 514/781, 788, 960, 961

[56] References Cited

U.S. PATENT DOCUMENTS

| | | | |
|---|---|---|---|
| 3,868,463 | 2/1975 | Remy | 424/330 |
| 3,907,999 | 9/1975 | Christy | 424/330 |
| 4,198,402 | 4/1980 | Ezer et al. | 424/232 |

FOREIGN PATENT DOCUMENTS

| | | |
|---|---|---|
| 0112061 | 6/1984 | European Pat. Off. |
| 0124027 | 11/1984 | European Pat. Off. |
| 0913984 | 9/1986 | European Pat. Off. |
| 0210661 | 2/1987 | European Pat. Off. |
| 1480188 | 7/1977 | United Kingdom |

OTHER PUBLICATIONS

Fonner, et al., "Pharmaceutical Dosage Forms", vol. 2, pp. 183–238 (1981).
Rankell et al., "Physics of Tablet Compression XV", vol. 57, No. 4 (1968) pp. 574–577.

Primary Examiner—Thurman K. Page
Assistant Examiner—Jyothsna A. Venkat
Attorney, Agent, or Firm—Birch, Stewart, Kolasch & Birch

[57] ABSTRACT

The invention relates to a process for the preparation of a tablet or dragée composition containing a moisture-, heat- and light-sensitive compounds having monoclinic crystalline structure as active ingredients, which comprises homogenizing the active ingredient with 0.2 to 1.5 parts by weight of an anhydrous alkaline earth metal salt and 0.5 to 2.5 parts by weight of microcrystalline cellulose calculated for the active ingredient and optionally with one or more pharmaceutically acceptable carrier(s) and/or additive(s) and compressing the homogeneous mixture obtained to tablets in a manner known per se and, if desired, coating the tablet thus obtained in a manner known per se.

5 Claims, No Drawings

PROCESS FOR THE PREPARATION OF A TABLET OR DRAGEE COMPOSITION CONTAINING A HEAT-, LIGHT- AND MOISTURE-SENSITIVE ACTIVE INGREDIENT HAVING MONOCLINIC CRYSTAL STRUCTURE

The invention relates to a process for the preparation of a tablet or dragée composition containing a heat-, light- and moisture-sensitive active ingredient having monoclinic crystal structure.

The process according to the invention is particularly useful for preparing a pharmaceutical composition having antiarrhythmic activity and containing as active ingredient an aminoguanidine derivative of the general formula (I),

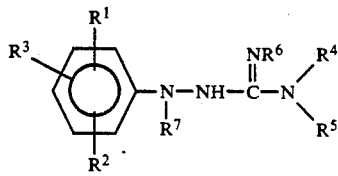

wherein
$R^1$, $R^2$ and $R^3$ stand independently from each other, for hydrogen, halogen or $C_{1-4}$ alkyl, nitro, $C_{1-4}$ alkoxy or trifluormethyl group;
$R^4$ and $R^5$ represent independently from each other, a $C_{1-4}$ alkyl group;
$R^6$ and $R^7$ represent, independently from each other, hydrogen or $C_{1-4}$ alkyl or $C_{2-4}$ alkenyl group
or their acid addition salts crystallizing in monoclinic system.

It is very difficult to prepare an oral dosage form such as tablet or dragée from substance having monoclinic crystal structure since the adhesion between the crystal plates is weak and the aggregation of granules is difficult to compress.

According to a method well-proved in the practice for tabletting monoclinic crystalline substances and having weak adhesive properties (e.g. phenylbutazone, phenacetin, barbiturates), the powdered mixture containing the active ingredient is pressed after wet granulation [H. A. Lieberman, L. Lachman: Pharmaceutical Dosage Forms, Tablets, Volume 2, Marcel Dkker, Inc., N.Y. (1981)]. In this case, the binding force needed to the tablet formation is provided by the binding agent introduced during the kneading whereas the optimum compressibility is ensured by the optimum porosity and flowability developed in the preparing procedure carried out in a suitable way.

The wet granulation cannot be carried out and the table formation can be realized only by direct compression or briquetting when the active ingredient crystallizes in monoclinic system and is also sensitive to moisture (e.g. salycilic acid derivatives). In this case the necessary adhesion is ensured partly by the solid binding agent introduced as a powder mixture and partly by the binding forces developed at the so-called active sites of the granule surfaces [A. S. Rankel et al.: J. Pharm. Soc. 57, 574 (1968)].

In cases of moisture- and light-sensitive substances, the tablets should be provided with a protective coat to prevent any damage during the storage. A tablet prepared by direct compression should possess an appropriate hardness in order to be useful for a further processing, e.g. dragée formation.

The hardness can be enhanced by increasing the force of compression, however, the density of tablet is increased and the porosity thereof is decrased by enhancing the force of compression. The disintegration of the tablet is deciseively influenced by the porosity since the higher the density of the tablet is, the slower is the penetration of the aqueous fluid thus, the dissolution of the active ingredient from a tablet of high density is very slow, the desired blood level of the acitve ingredient can be achieved only after a long period and the bioavailability of the active ingredient is also low.

During compression a heat effect is developed by the friction of the granules, whereby the heat-sensitive active ingredients are usually decomposed thus, a direct compression or briquetting cannot be employed in these cases.

As a consequence, it is a very difficult task to formulate monoclinic crystalline compounds simultaneously being sensitive to moisture, heat and light effects to tablet composition. No literature reference has been found for the solving of this problem.

The aim of the present invention is to work out a composition, which is useful for the preparation of a tablet or dragée core from monoclinic moisture-, heat- and light-sensitive compounds by compression. A further aim of the present invention is to prepare a tablet or dragée composition making possible the rapid absorption of the active ingredient as well as the development of high blood levels after taking the composition and resulting in a high bioavailability of the active ingredient.

Surprisingly, it has been found that the above aims can be achieved by adding 0.2 to 1.5 parts by weight of an anhydrous alkaline earth metal salt and 0.5 to 2.5 parts by weight of microcrystalline cellulose calculated form the active ingredient, to the moisture-, heat- and light-sensitive active ingredient having monoclinic crystalline structure.

Thus, the present invention relates to the preparation of a tablet or dragée composition from moisture-, heat- and light-sensitive active ingredient having monoclinic crystalline structure, which comprises homogenizing the active ingredient with 0.2 to 1.5 parts by weight of an anhydrous alkaline earth metal salt and 0.5 to 2.5 parts by weight of microcrystalline cellulose calculated for the active ingredient as well as, if desired, with one or more pharmaceutically acceptable carrier(s) and/or additive(s) and compressing the homogeneous mixture thus obtained to tablets in a manner known per se and, if desired, coating the tablet obtained in a manner known per se.

The invention is based on the recognition that a tablet with suitable breaking strength can be prepared by using relatively low pressure of 150 to 200 MPa, when a tablet is compressed in such a way that a defined amount of an anhydrous alkaline earth metal salt and microcrystalline cellulose are added to the monoclinic moisture-, heat- and light-sensitive active ingredient. In this case, no increase in the free energy occurs at the binding sites, which could induce a chemical change, i.e. the decomposition of the active ingredient since the displacement at the binding sites of the mobile anions being present in the crystal structure of the active ingredient is inhibited by the alkaline earth metal salt and simultaneously, a tablet can be obtained which is suitably solid for coating, conveniently disintegrates in the stomach and advantageously releases the active ingredient.

In the process of the invention, e.g. calcium or magnesium hydrogen phosphate, calcium or magnesium dihydrogen phosphate or sulfate or carbonate may be used as anhydrous alkaline earth metal salts.

Suitable pharmaceutically acceptable carriers in the preparation of the invention are e.g. talc, maize starch, magnezium stearate, colloidal silica (Aerosil 200), lactose, glucose, mannitol or the like.

Suitable additives are e.g. one or more binding agent(s), antioxidant(s) disintegrating or flowability-promoting additive(s).

Useful binding agents are e.g. polyvinylpyrrolidone, vinylpirrolidone/vinyl acetate copolymer (Luwiskol VA 64) or polyethylene glycols.

Useful antioxidants are e.g. ascorbic acid or sodium disulfide.

The active ingredient content of the composition according to the invention may be varied between broad limits depending from the nature of the active ingredient, type of the disease to be treated, dose of the active ingredient to be used and the like. The active ingredient content of the composition is preferably 0.5 to 50% by weight.

The composition according to the invention contains the alkaline earth metal salt and microcrystalline cellulose in an amount of 2 to 90% by weight, preferably in an amount of 30 to 75% by weight.

The tablets are prepared by homogenizing the ingredients and then by compressing the homogeneous mixture obtained by using a pressure of 150 to 200 MPa in a known manner.

If desired, the tablet may be provided with a coat.

The coat has to satisfy two demands: on the one hand, the active ingredient should be protected against the harmful effect of light and air moisture and on the other hand, a suitable dissolution of the active ingredient has simultaneously to be ensured.

Since the active ingredient is sensitive to moisture, no aqueous system can be used and an organic solvent can only by considered for coating.

The coat conveniently contains a hydrophilic component (such as polyethylene glycol, water-soluble cellulose ethers or vinylpirrolidone/vinyl acetate copolymer) and a hydrophobic component (ethylcellulose or acrylate/metacrylate ester copolymer). The weight ratio of hydrophilic components to the hydrophobic components is preferably 1:1 to 1:1.5.

Pharmaceutically acceptable organic solvents being capable to dissolve the components of the coat, such as alcohols and ketones, e.g. ethanol, isopropanol, acetone or their mixtures may be used as solvents for coating material.

The mixture containing ethanol/acetone or isopropanol/acetone in a volume ratio of 1:0.2 to 1:1.5 is preferred as solvent.

The coating process is carried out by using a suspension prepared with an organic solvent containing the hydrophilic and hydrophobic substances and optionally other additives (e.g. light-protective dyes such as an iron oxide pigment) in a known manner.

The process according to the invention is particularly useful for preparing an antiarrhythmic active pharmaceutical composition composition containing as active ingredient an aminoguanidine derivative of the general formula (I), wherein $R^1$, $R^2$ and $R^3$ stand independently from each other, for hydrogen, halogen or $C_{1-4}$ alkyl, nitro $C_{1-4}$ alkoxy or trifluormethyl group;

$R^4$ and $R^5$ represent independently from each other, a $C_{1-4}$ alkyl group;

$R^6$ and $R^7$ represent, independently from each other, hydrogen or $C_{1-4}$ alkyl or $C_{2-4}$ alkenyl group or their acid addition salts crystallizing in monoclinic system.

The aminoguanidine derivatives of general formula (I) and their acid addition salts are moisture-, light-and heat-sensitive and are transformed to vivid red-coloured phenylazoformamidine derivatives by an auto-oxidation reaction.

When the hydrochloride of 1-(2,6-dimethylphenyl)-4,4'-dimethylaminoguanidine being within the scope of the general formula (I) is subjected to a wet granulation according to known processes and then compressed to tablets (shown in Example 1), then the active ingredient of the compsition significantly decomposes within a short time interval (e.g. 10 days). The same decomposition of the active ingredient has not been observed on compositions prepared according to the invention: the composition remained stable during a longer time of storage and even in the case of a higher moisture content.

Based on clinical investigations, on using 1-(2,6-dimethylphenyl)-4,4'-dimethylaminoguanidine hydrochloride being within the scope of the general formula (I) as active ingredient of the composition according to the invention, the half life measured in the blood increased from 2.4 hours to 3.2 hours in comparison to an injectable composition containing the same active ingredient, whereas the relative bioavailability of the active ingredient proved to be about 80%.

The process according to the invention is illustrated in detail by the following non limiting Examples.

1-(2,6-Dimethylphenyl)-4,4'-dimethylaminoguanidine hydrochloride was used as active ingredient in all these Examples. The amounts given in the Examples mean parts by weight (pbw) in each case when it is not noted otherwise.

COMPARATIVE EXAMPLE 1

| Ingredients | Amounts |
| --- | --- |
| Active ingredient | 500 |
| Lactose | 1005 |
| Maize starch | 900 |
| Microcrystalline cellulose | 420 |
| Polyvinylpyrrolidone | 85 |
| Ascorbic acid | 30 |
| Magnesium stearite | 20 |
| Talc | 40 |

The active ingredient was admixed with maize starch, microcrystalline cellulose and lactose. Polyvinylpyrrolidone and ascorbic acid were dissolved in 800 ml of ethanol and the homogeneous mixture was granulated with the latter solution. After drying, the granulate was homogenized with the substances of the outer phase and then compressed to flat edge tablets weighing 300 mg each by using a compression pressure of 100 to 150 MPa. The breaking strength of the tablets was 50 to 75N.

The tablets obtained were subjected to storage experiments carried out in the presence of moisture and heat as well as light load. According to our observations the colour of the tablet became deeper and a decomposition product of 1 to 2% by weight could be detected at a temperature of 60° C. or at room temperature in the presence of a relative moisture content of 80% during 10 days. This decomposition process could not be prevented by ascorbic acid.

EXAMPLE 2

| Ingredients | Amounts |
|---|---|
| Active ingredient | 500 |
| Lactose | 810 |
| Maize starch | 900 |
| Colloidal silicon dioxide | 15 |
| Polyvinylpyrrolidone | 85 |
| Microcrystalline cellulose | 600 |
| Ascorbic acid | 30 |
| Talc | 40 |
| Magnesium stearate | 20 |

The sieved components with the prescribed particle size were carefully homogenized and the aggregation of granules obtained was compressed to biconvex tablets of 10 mm in diameter weighing 300 mg each by using a compression pressure of 150 MPa on a rotating tablet machine.

The tablets possess a breaking strength of 40 to 50N.

EXAMPLE 3

| Ingredients | Amounts |
|---|---|
| Active ingredient | 1000 |
| Maize starch | 660 |
| Anhydrous calcium hydrogen phosphate | 900 |
| Microcrystalline cellulose | 1540 |
| Vinylpyrrolidone/vinyl acetate copolymer | 160 |
| Talc | 120 |
| Ascorbic acid | 60 |
| Magnesium stearate | 40 |
| Colloidal silica | 20 |

The sieved components with the prescribed particle size were carefully homogenized and the aggregation of granules obtained was compressed to biconvex tablets of 9 mm in diameter weighing 300 mg each by using a compression pressure of 150 MPa on a rotating tablet machine.

The tablets possess a breaking strength of 50 to 80 N.

The dragée scores obtained as described above were coated with a suspension containing the ingredients listed below in a pan suitable for film coat formation.

| Ingredients | g |
|---|---|
| Ethylcellulose | 56 |
| Vinylpyrrolidone/vinyl acetate copolymer | 56 |
| Talc | 68 |
| Magnesium stearate | 10 |
| Titanium dioxide | 4 |
| Yellow iron oxide pigment | 6 |
| Ethanol | 1080 |
| Acetone | 1000 |

The tablet prepared as described above was stored in a relative moisture content of 75% and 95%, respectively for 12 months. The results are shown in Table I.

TABLE I

| | Relative moisture content | | | |
|---|---|---|---|---|
| | 75% | | 95% | |
| Months | mg/tablet | decomp. % | mg/tablet | decomp. % |
| 0 | 49.85 | 0 | 0 | 0 |
| 1 | 49.82 | 0.09 | 50.17 | 0.2 |
| 2 | 49.22 | 0.10 | 49.82 | 0.1 |
| 4 | 49.73 | 0.90 | 49.37 | 1.7 |
| 12 | 49.98 | 0.05 | — | — |

In order to determine the heat-stability, the tablets were stored at 24°, 40°, 50° or 60° C., respectively for 12 months. The results are shown in Table II.

TABLE II

| | Temperature | | | | | | | |
|---|---|---|---|---|---|---|---|---|
| Time of | 24° C. | | 40° C. | | 50° C. | | 60° C. | |
| storage months | mg/tab. | dec. % | mg/tab. | dec. % | mg/tab. | dec. % | mg/tab. | dec. % |
| 0 | — | — | — | — | — | — | — | — |
| 1 | — | — | — | — | 49.06 | 0.25 | 49.04 | 0.09 |
| 2 | — | — | 48.88 | 0.13 | 48.35 | 0.13 | 48.23 | 0.13 |
| 4 | — | — | 48.06 | 0.40 | 48.00 | 0.60 | 47.32 | 0.13 |
| 8 | 52.32 | 0.35 | 49.10 | — | — | — | — | — |
| 12 | 51.06 | 0.45 | — | — | — | — | — | — |

The absorption of the active ingredient from the tablet prepared as described above was investigated in dogs. The composition showed an absorption coefficient ($k_a$) of 0.9 to 1.6 $h^{-1}$ and an elimination coefficient ($k_e$) of 0.20 to 0.25 $h^{-1}$, i.e. the values indicate a rapid absorption.

The preceding results were supported by pharmacokinetic examinations carried out in the human I phase clinical trials. A value of 1.4 $h^{-1}$ was obtained for the absorption coefficient ($k_a$) in the human trials. The relative bioavailabilty calculated from the AUC values proved to be 80%. This value can be considered to be very high as a part of the antiarrhytmic reference drugs (e.g. aminodarone) were not absorbed and a bioavailability of 40 to 70% has only been achieved in case of other drugs (e.g. quinidine, lidocaine) [P. G. Welling et al.: Pharmacokinetics of Cardiovascular, Central Nervous System and Antimicrobial Drugs, London, (1985)].

EXAMPLE 4

| Ingredients | Amounts |
|---|---|
| Active ingredient | 1000 |
| Maize starch | 600 |
| Anhydrous calcium hydrogen phosphate | 900 |
| Microcrystalline cellulose | 1800 |
| Vinylpyrrolidone/vinyl acetate copolymer | 160 |
| Talc | 120 |
| Ascorbic acid | 60 |
| Magnesium stearate | 40 |
| Colloidal silica | 20 |

After crushing and sieving to the desired particle size, the components were carefully homogenzied, then the aggregation of granules obtained was compressed to biconvex tablets of 11 mm in diameter weighing 430 g each by using a compression pressure of 200 MPa on a rotating tablet machine.

The tablets possess a breaking strength of 80 to 100N. The dragée scores were uniformly coated in an automated dragée-forming apparatus with a suspension containing the following ingredients.

| Ingredients | g |
|---|---|
| Acrylic acid/metacrylic acid copolymer | 60 |
| Polyethylene glycol 600 | 40 |
| Talc | 80 |
| Magnesium stearate | 10 |
| Titanium dioxide | 4 |
| Yellow iron oxide pigment | 6 |
| Isopropanol | 1000 |
| Acetone | 900 |

EXAMPLE 5

| Ingredients | Amount |
|---|---|
| Active ingredient | 2000 |
| Maize starch | 110 |
| Anhydrous calcium hydrogen phosphate | 450 |
| Microcrystalline cellulose | 1200 |
| Polyvinylpyrrolidone | 200 |
| Talc | 120 |
| Sodium disulfite | 50 |
| Magnesium stearate | 40 |
| Colloidal silica | 30 |

The sieved components with the prescribed particle size are carefully homogenzied, then the aggregation of granules obtained is compressed to biconvex tablets of 11 mm in diameter weighing 420 mg each by using a compression pressure of 150 MPa on a rotating tablet machine.

The tablets possess a breaking strength of 90 to 100N.

The tablet scores are uniformly coated in an automated dragée-forming apparatus with a suspension containing the following ingredients:

| Ingredients | g |
|---|---|
| Ethylcellulose | 58 |
| Hydroxypropylcellulose | 50 |
| Talc | 70 |
| Magnesium stearate | 11 |
| Titanium dioxide | 3 |
| Red iron oxide pigment | 8 |
| Ethanol | 1800 |
| Acetone | 400 |

What is claimed is:

1. A process for the preparation of a tablet or dragée composition containing a moisture-, heat- and light-sensitive aminoguanidine derivative of formula (I), having a monoclinic crystalline structure,

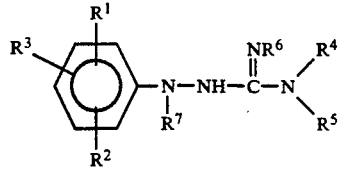

wherein
$R^1$, $R^2$ and $R^3$ stand independently from each other, for hydrogen, halogen or $C_{1-4}$ alkyl, nitro, $C_{1-4}$ alkoxy or trifluoromethyl group,
$R^4$ and $R^5$ represent independently from each other, a $C_{1-4}$ alkyl group;
$R^6$ and $R^7$ represent, independently from each other, hydrogen, $C_{1-4}$ alkyl or $C_{2-4}$ alkenyl group; or a pharmaceutically acceptable acid addition salt thereof; the process comprising the steps of:
homogenizing the formula (I) aminoguanadine derivative with 0.2 to 1.5 parts by weight of an anhydrous alkaline earth metal salt selected from the group consisting of a hydrogen phosphate salt, a dihydrogen phosphate salt, a hydrogen carbonate salt, a carbonate salt and a sulfate salt of calcium and magnesium, 0.5 to 2.5 parts by weight of microcrystalline cellulose, 0.05 to 0.3 parts by weight of a binding material selected from the group consisting of polyvinylpyrrolidone and vinylpyrrolidone/vinyl acetate copolymer, 0.01 to 0.04 parts by weight of a glidant which is colloidal silicone dioxide, and 0.01 to 0.1 parts by weight of an antioxidant selected from the group consisting of ascorbic acid and sodium disulfide calculated for the active ingredient, and one or more pharmaceutically acceptable antiadhesive, lubricating and filling additive(s);
compressing the homogeneous mixture obtained to tablets; and
coating the tablets thus obtained.

2. A process as claimed in claim 1, wherein the active ingredient is 1-(2,6-dimethylphenyl)-4,4'-dimethylaminoguanidine hydrochloride.

3. A process as claimed in claim 1, which comprises: homogenizing as the active ingredient 1-(2,6-dimethylphenyl)-4,4'-dimethyl aminoguanidine hydrochloride with 0.2 to 1.5 parts by weight of anhydrous calcium hydrogen phosphate and 0.5 to 2.5 parts by weight of microcrystalline cellulose calculated for the active ingredient.

4. A process as claimed in claim 1, wherein the active ingredient is present in an amount of 0.5 to 50% by weight in the tablet or dragée composition prepared.

5. A process as claimed in claim 1, wherein the anhydrous alkali earth metal salt and the microcrystalline cellulose are present in an amount of 2 to 90% by weight in the tablet or dragée composition prepared.

* * * * *